United States Patent [19]

Bhatia

[11] Patent Number: 5,043,458

[45] Date of Patent: * Aug. 27, 1991

[54] ONE-STEP CONTINUOUS PROCESS FOR PREPARING CYCLIC ESTERS

[75] Inventor: Kamlesh K. Bhatia, Newark, Del.

[73] Assignee: E. I. Du Pont de Nemours and Company, Wilmington, Del.

[*] Notice: The portion of the term of this patent subsequent to May 30, 2006 has been disclaimed.

[21] Appl. No.: 521,063

[22] Filed: May 3, 1990

[51] Int. Cl.[5] ............................................ C07D 319/00
[52] U.S. Cl. ..................................... 549/274; 549/518
[58] Field of Search ................................ 549/274, 518

[56] References Cited

U.S. PATENT DOCUMENTS

| | | | |
|---|---|---|---|
| 3,457,280 | 7/1969 | Schmitt et al. | 549/274 |
| 4,835,293 | 5/1989 | Bhatia | 549/274 |

Primary Examiner—C. Warren Ivy
Assistant Examiner—Ba K. Trinh
Attorney, Agent, or Firm—Charles E. Krukiel

[57] ABSTRACT

A continuous, gas-assisted atmospheric process for preparing cyclic esters of alpha-hydroxycarboxylic acids, such as lactide, which comprises feeding the reactants into a reactor having means for introducing an inert gas at the operating temperature, forming a reaction mass having cyclic esters in the reactor, passing a flow of said inert gas through said reactor whereby cyclic esters are swept from the reaction mass into a gaseous product stream, and recovering the cyclic esters therefrom.

12 Claims, No Drawings

ONE-STEP CONTINUOUS PROCESS FOR PREPARING CYCLIC ESTERS

FIELD OF THE INVENTION

This inventions relates to a continuous process for preparing cyclic esters by thermolysis of an alpha-hydroxycarboxylic acid or a salt thereof. More particularly the invention relates to a gas-assisted atmospheric pressure process that provides for rapid production of the cyclic esters, in particular, lactide.

BACKGROUND OF THE INVENTION

The preparation of cyclic esters of alpha-hydroxycarboxylic acids is an old and much studied process. Heretofore, the preparation has been conducted in two distinct batch steps involving first preparing an oligomer of the hydroxycarboxylic acid, i.e., a relatively short-chain condensation polymer thereof, then heating the polymer under reduced pressure to generate the desired cyclic ester. Gruter et al., U.S. Pat. No. 1,095,205 (1914); Lowe, U.S. Pat. No. 2,668,162 (1954); Bhatia, U.S. Pat. No. 4,835,293 (1989); Bellis U.S. Pat. No. 4,727,163 (1988); Müller, Ger. Pat. Applications 3632103 and 3708915 (1988). Such processes spanning over 70 years of technology suffer in that they require hours of reaction time at high temperatures for the preparation of the polymeric intermediate and its thermolysis to the cyclic ester. Further, the rather long residence times at the high temperatures employed often results in side reactions, leading, for example, to unwanted isomers, charring of the polymer and consequently difficult to handle reactor heels.

It is an object of this invention to provide a novel essentially single-step process for the rapid conversion of an alpha-hydroxycarboxylic acid, such as lactic acid, to a cyclic ester, such as lactide.

Another object is to provide such a process that enables continuous production of a cyclic ester such as lactide directly and rapidly from the corresponding alpha-hydroxycarboxylic acid in a single reaction zone without need to separately prepare an oligomer of the acid as intermediate to the cyclic ester.

SUMMARY OF THE INVENTION

A continuous process for preparing a cyclic ester having the formula,

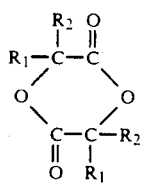

wherein $R_1$, and $R_2$ are independently a hydrogen or an aliphatic hydrocarbyl radical having 1 to 6 carbon atoms, which process comprises (i) continuously feeding a reactant feed stream containing at least one of (a) an alpha-hydroxycarboxylic acid, $HOCR_1R_2CO_2H$, and (b) a salt of (a) into the inlet end of a reactor having an inlet end and a product outlet end and an inlet for introducing a substance that is gaseous and non-reactive at the operating temperature; while (ii) maintaining the reaction zone at a temperature and pressure effective to result in the formation of a fluid reaction mass containing cyclic ester;

(iii) continuously passing a flow of said substance that is gaseous and non-reactive at the reaction temperature through said inlet, the flow being sufficiently large to sweep cyclic ester from the reaction mass and form a gaseous product stream containing the gas and cyclic ester;

(iv) removing the product stream of (iii) from the reaction zone; and (v) recovering the cyclic ester from the product stream.

In a preferred embodiment the process is carried out at at least about atmospheric pressure, as disclosed in Bhatia U.S. Pat. No. 4,835,293.

In another embodiment the feed system is liquid, preferably preheated so as to reduce the heat load on the reactor.

In another more specific embodiment the reactant feed rate and the product stream removal rate are coordinated so as to establish a steady state in that the quantity of reaction mass is maintained substantially constant within the reaction zone.

In particular, the process, broadly and more specifically, is directed to the one-step preparation of lactide, including L-lactide and D-lactide in high yields and high state of purity at high production rates, starting with lactic acid or a mixture thereof with an oligomer of lactic acid formed during the process.

The invention is based on the discovery that the conversion of an alpha-hydroxycarboxylic acid such as lactic acid to the corresponding cyclic ester, e.g., lactide, proceeds more rapidly than heretofore. The overall reaction must be carried out sufficiently hot and rapidly with a gaseous substance preferably employed to assist in stripping the cyclic ester from the reaction mass substantially as soon as it is formed. Preferably, the feed and cyclic ester removal rates are coordinated and adjusted as needed to maintain a substantially constant quantity of reaction mass in the reaction zone, i.e., a steady state.

It is believed the reaction proceeds to form lactide directly from lactic acid itself or from an oligomer thereof. Thus, the invention process offers numerous advantages over the art. It substantially reduces the time required for converting an alpha-hydroxycarboxylic-based feed material as defined into the desired cyclic ester. In contrast to the prior processes, which require hours for such conversion, the subject process can produce a cyclic ester such as lactide in much less time. As a consequence of the continuous feed, product take-off and gas sweeping features, in combination with the effective reaction temperatures, the hold-up of reaction mass can be minimized so that loss of potential cyclic ester yield through degradation and charring of the reaction mass is also minimized. The invention process is therefore capable of providing high yields of a cyclic ester such as lactide through recycle of unreacted starting material.

Further, operating at pressures of about atmospheric reduces investment and operating costs, by eliminating the costly equipment required for maintaining the low reduced pressures utilized in the art. It also provides for a safer operation, particularly in combination with a cyclic ester stripping gas. The stripping gas eliminates the potential for explosive atmospheres within the reactor that can result from air leaks, especially at reduced pressures.

DETAILED DESCRIPTION OF THE INVENTION

In general, the process is conducted by continuously introducing an alpha-hydroxycarboxylic acid or a heat-dissociable amine salt thereof into a reaction zone preheated to a temperature effective to convert the carboxylic acid, and/or salt thereof to a cyclic ester. Substantially simultaneously, a substantially constant flow of a cyclic ester-stripping agent as defined is passed into the reaction mass to bring it into intimate contact with the reaction mass and to carry reaction products away from the reaction zone, the product stream removed from the reaction zone contains the cyclic product along with other reaction products, for example, in the case of a lactic acid feed, the free water, the water of reaction and unconverted lactic acid. The cyclic ester may be recovered by any of the methods known to the art, including solvent-scrubbing. One such solvent-scrubbing method is disclosed in Bhatia U.S. Pat. No. 4,835,293, which disclosure is incorporated herein by reference. Unreacted alpha-hydroxy acid recovered from the reaction product stream can be recycled to the reaction zone as well as any oligomeric purge from the reactor, either alone or in conjunction with fresh starting material.

The alpha-hydroxycarboxylic-based feed stream material includes:

(a) alpha-hydroxycarboxylic acids, $HOCR_1R_2CO_2H$, where $R_1$ and $R_2$ can independently be hydrogen or a $C_1-C_6$ aliphatic hydrocarbyl radical;

(b) a salt, for example, an alkali metal salt or a heat-dissociable ammonium or amine salt, $HOCR_1R_2CO_2HA$, where A is ammonia or an amine and the salt is dissociable into the acid, (a), and the nitrogen base at the operating temperatures.

Preferably, $R_1$ and $R_2$, when other than H in the above formulas, are $C_1-C_4$ alkyl groups. More preferably, $R_1$ and $R_2$ are H or methyl, as in glycolic acid ($R_1=R_2=H$) and lactic acid ($R_1=H$, $R_2=CH_3$).

The amine salt of the alpha-hydroxycarboxylic acid can be any such salt that is dissociable into the acid and the amine at process temperatures. Preferably it will be a salt of a tertiary amine, more preferably aliphatic, such as trimethylamine, triethylamine, dimethylethylamine, tributylamine or the like.

The invention process will be conducted in the presence of a catalyst, carried in the feed stream along with the hydroxycarboxylic-based reactant or incorporated directly into the reaction mass. The catalyst can be any of those known in the art for promoting condensation of the alpha-hydroxycarboxylic component to oligomers and/or for promoting cyclic ester formation. The catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn(II) carboxylates, especially those that are soluble in the feed stream and the resulting reaction mixture, exemplified by Sn bis (2-ethylhexanoate), commonly referred to as stannous octoate.

The catalyst will be employed in catalytically effective amounts, which can vary widely depending upon the particular feed material employed and reaction conditions. The optimum catalytically effective amounts for any particular system can readily be determined through trial runs. For example, with a Sn (II) octoate the quantity will generally be such that the reaction mass will contain from about 0.1 to 1.5% by weight, preferably from about 0.3 to 0.7% by weight. The gaseous agent for entraining/carrying/sweeping the cyclic ester and water-of-reaction out of the reaction mixture and out the reactor may be any substance that is gaseous, stable and non-reactive at the operating temperatures and pressures and is inert to the starting material, reaction mass components and reaction products. It may be normally gaseous, such as nitrogen, argon, carbon monoxide or dioxide or low molecular weight hydrocarbon. It may be normally non-gaseous but gaseous at reaction temperature and pressure.

Preferred is nitrogen for its inertness and ready availability. Preferably the inert gas will be preheated to the operating temperature and will be injected below the surface of the reaction mass in the reaction zone; for example, below the agitator of a stirred tank reactor or at the bottom of a vertically disposed reactor.

The flow rate of the gas should be sufficiently high so as not to limit the cyclic ester production rate. If the flow rate is too low the yield of cyclic ester may be adversely affected and its production rate limited since the gas functions importantly to carry the cyclic ester as vapor out of the reactor. While the optimum flow may vary with any particular combination of feed material, catalyst, reaction temperature and reactor design and configuration, it will normally be in the range of from about 5 to 20 moles per mole of feed, preferably from 7 to 15 moles per mole of feed.

It will also be noted that the gaseous component helps maintain the reaction mixture in the reaction zone well-mixed, as well as to remove volatiles therefrom, and in this way helps to avoid the occurrence of localized "hot spots", i.e. zones of unduly high temperatures which could otherwise result in unwanted and yield-lowering degradation and charring of the reaction mass. Suitably effective temperatures for converting monomeric alpha-hydroxy carboxylic component, i.e., acid or ammonium or amine salt to cyclic ester can vary widely, but normally will be in the range of from about 170. to 270.C, preferably in the range of from about 190. to 235.C, and in the case of lactide production 195 to 220.C.

The pressure may vary from sub-atmospheric to atmospheric and super-atmospheric. Preferably it is about atmospheric, plus a small back pressure exerted on the product stream by the downstream equipment which should be designed to keep the back pressure as low as practical, for example, to keep the back pressure as low as 5 psig.

The reactor design and configuration is not critical provided it provides a reaction zone that permits the formation and accumulation of an in situ produced fluid reaction mass, has means for introducing a gaseous cyclic ester-stripping agent into the reaction zone such that it intimately contacts the reaction mass and has means for removing a gaseous stream containing cyclic ester. Thus the reactor may be a stirred tank equipped with gas sparging means, preferably one which admits the gas directly under the agitator. The reactor may be of any design known in the art for effective intimate gas-liquid contact, such as a bubble column or plate column, or a spray reactor or a film reactor, again with means for introducing the gaseous component such that it intimately contacts the spray or film constituting the reaction mass. Likewise the product stream recovery and processing system may be any of those known to the art. One such reactor and product recovery system is disclosed in Bhatia U.S. Pat. No. 4,835,293 which disclosure is incorporated herein by reference.

If desired alpha-hydroxycarboxylic acids can be fed to the reactor as solution, say in water, acetone or other suitable solvent. Lactic acid, for example, is commercially available as concentrated aqueous solutions which may be fed directly to the reaction zone in the method of the invention.

EXAMPLES

Examples 1-2 below were conducted in a stirred reactor equipped with a feed inlet, a gaseous product stream outlet and a gas sparging device for introducing $N_2$ gas as more fully described in Bhatia U.S. Pat. No. 4,835,293, including FIG. 1 therein.

EXAMPLE 1

376.4 gms of 88% L-lactic acid containing 2 gms of stannous octoate catalyst was charged to a reactor, preheated to 217° C. to reduce the heating time, while a stream of $N_2$ preheated to 135° C. was flowing through the reactor at a rate of 0.1 SCFM to facilitate removal of the free water present in the lactic acid and the water of condensation of lactic acid to an oligomer. Charging the preheated reactor with lactic acid dropped the temperature to 93.C, but it was quickly heated up to start removing water. Water removal was continued as the reactor temperature continued to increase. After only 20 minutes most of the water was removed, as the reactor temperature reached 178° C., lactide started to evolve and was seen freezing out from the $N_2$ stream in the water cooled condenser connected to the reactor.

Thereafter, lactic acid could be fed continuously with continuous generation of lactide, as described more specifically in the following Example.

EXAMPLE 2

106.9 gms of 88% L-lactic acid containing 0.25% weight stannous octoate as catalyst was charged to the reactor preheated to 215° C. and water removed as in Example 1. In 19 minutes, 40.2 gms of water plus the lactic acid that volatilized were collected as condensate leaving 66.7 gms of oligomer in the reactor.

A continuous feed of 88% lactic acid containing 0.25% weight catalyst, preheated to 68° C., was then started and the reaction products stripped away with the $N_2$ stream were recovered by scrubbing it with acetone. The feed rate, $N_2$ rate and reactor temperature were adjusted during the next 73 minutes so as to arrive at a nearly steady state operating conditions. During this period a total of 180 gms of lactic acid feed was consumed and 25 gms of oligomer reactor mass was drained from the reactor so that the oligomer level was about the same as when starting the continuous feed.

After the above adjustment period to achieve a nearly steady operation, the acetone solution was drained from the scrubber and fresh acetone changed to scrubber. Lactic acid containing 0.25% catalyst was fed to the reactor for the next 20 minutes at a rate of 3 gms/min while the nitrogen heated to 164° C. was sparged at a rate of 0.3 SCFM. The reactor temperature during this period ranged between 208° and 221° C. The reaction was then stopped and the reactor contents as well as the acetone solution from the scrubber were drained.

The reaction mass, 61 gms, was quite fluid and light amber in color in sharp contrast to the highly viscous and blackish reactor heels obtained in the conventional prior art processes.

The acetone solution was concentrated by vacuum stripping the acetone and then adding chilled water so as to precipitate the lactide product and retain the unconverted acid in the water. The L-lactide product was filtered, washed twice with cold water and dried. It weighed 35.6 gms. The product was pure white, crystalline L-lactide and found to be 97.24% pure by differential scanning calorimetry (DSC).

The filtrate and washings from the above operation were combined and evaporated under vacuum to obtain 26 gms of unconverted lactic acid.

Thus, about 55% of the lactic acid fed was converted to lactide. The recovered unconverted acid, as well as the fluid reaction mass, could be recycled to obtain a high overall yield.

Based on the 61 grams of reaction mass drained from the reactor at the end of the reaction and the 3 grams per minute feed rate of the acid, the reaction residence time is calculated to be about 20 minutes.

What is claimed is:

1. A continuous process for preparing a cyclic ester having the formula,

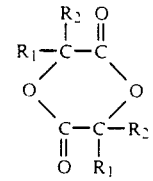

wherein $R_1$ and $R_2$ are independently hydrogen or an aliphatic hydrocarbyl radical having 1 to 6 carbon atoms, which process comprises
   (i) continously passing a feed stream containing an alpha-hydroxycarboxylic acid, $HOCR_1R_2CO_2H$, or a salt thereof into the inlet end of a reaction zone having an inlet end and an outlet end; while
   (ii) maintaining the reaction zone at a temperature and pressure effective to result in a fluid reaction mass containing cyclic ester;
   (iii) continuously passing a flow of substance that is gaseous and non-reactive through the reaction mass, the flow being sufficiently large to sweep cyclic ester from the reaction mass and form a gaseous product stream comprising the gas and cyclic ester;
   (iv) removing the product stream of (iii) from the reactor; and
   (v) recovering the cycle ester from the product stream.

2. The process of claim 1 wherein the reaction zone is maintained at pressure of at least about atmospheric pressure.

3. The process of claim 2 wherein the feed stream is liquid and the reaction mass is liquid.

4. The process of claim 2 wherein the reaction mass contains a catalyst effective to promote the condensation of the alpha-hydroxy acid or ammonium or amine salt thereof to an oligomer and to effect conversion of the condensation product to a cyclic ester.

5. The process of claim 3 wherein the feed stream contains a catalyst as in claim 4.

6. The process of claim 5 wherein the reaction zone temperature is in the range of from about 170° to about 270° C.

7. The process of claim 6 wherein the temperature is in the range of from about 190° C. to about 235° C.

8. The process of claim 5 or claim 6 wherein the feed stream is preheated.

9. The process of claim 2 wherein (a) the feed stream is fed at a first rate and the product stream is removed at a second rate, said rates being coordinated and adjusted as necessary to establish a steady state characterized by a substantially constant quantity of reaction mass within the reaction zone, and (b) the feed and product stream rates are maintained to provide a substantially constant rate of production of cyclic ester.

10. The process of claim 2 wherein the feed stream hydroxy acid component is an alpha-hydroxycarboxylic acid.

11. The process of claim 10 wherein the hydroxycarboxylic acid is lactic acid and the cyclic ester is lactide.

12. The process of claim 1 wherein the acid is L-lactic acid and the cyclic ester is L-lactide.

* * * * *